(12) United States Patent
Erramilli et al.

(10) Patent No.: US 10,378,044 B1
(45) Date of Patent: Aug. 13, 2019

(54) METHODS FOR INCREASING THE MOLECULAR SPECIFICITY OF A NANOSENSOR

(71) Applicant: FemtoDx, Beverly Hills, CA (US)

(72) Inventors: Shyamsunder Erramilli, Quincy, MA (US); Pritiraj Mohanty, Los Angeles, CA (US)

(73) Assignee: FemtoDx, Beverly Hills, CA (US)

( * ) Notice: Subject to any disclaimer, the term of this patent is extended or adjusted under 35 U.S.C. 154(b) by 267 days.

(21) Appl. No.: 14/504,205

(22) Filed: Oct. 1, 2014

Related U.S. Application Data

(60) Provisional application No. 61/885,235, filed on Oct. 1, 2013.

(51) Int. Cl.
*G01N 33/553* (2006.01)
*C12Q 1/6825* (2018.01)
*C12Q 1/6837* (2018.01)
*G01N 27/414* (2006.01)

(52) U.S. Cl.
CPC ......... *C12Q 1/6825* (2013.01); *C12Q 1/6837* (2013.01); *G01N 27/4145* (2013.01); *G01N 33/553* (2013.01)

(58) Field of Classification Search
None
See application file for complete search history.

(56) References Cited

U.S. PATENT DOCUMENTS

| | | | | | |
|---|---|---|---|---|---|
| 4,562,157 | A | * | 12/1985 | Lowe | C12Q 1/003 324/71.1 |
| 4,778,769 | A | * | 10/1988 | Forrest | G01N 33/5438 204/403.14 |
| 6,274,323 | B1 | * | 8/2001 | Bruchez | B82Y 15/00 435/6.11 |
| 7,956,427 | B2 | * | 6/2011 | Lieber | B82Y 10/00 257/414 |
| 8,940,548 | B2 | * | 1/2015 | Khater | B82Y 10/00 436/524 |
| 9,645,135 | B2 | * | 5/2017 | Shin | G01N 27/4146 |
| 2013/0217049 | A1 | * | 8/2013 | Anderson | G01N 33/54393 435/7.94 |

* cited by examiner

*Primary Examiner* — Christopher L Chin
(74) *Attorney, Agent, or Firm* — Wolf, Greenfield & Sacks, P.C.

(57) ABSTRACT

Systems and methods for detecting a target species using a semiconductor nanosensor are generally described.

3 Claims, 13 Drawing Sheets

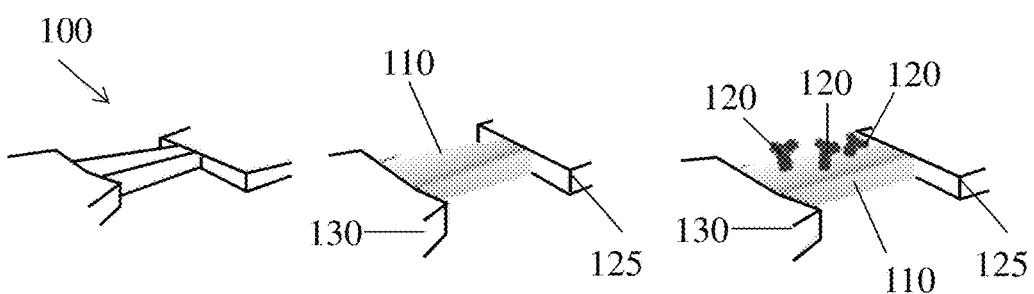
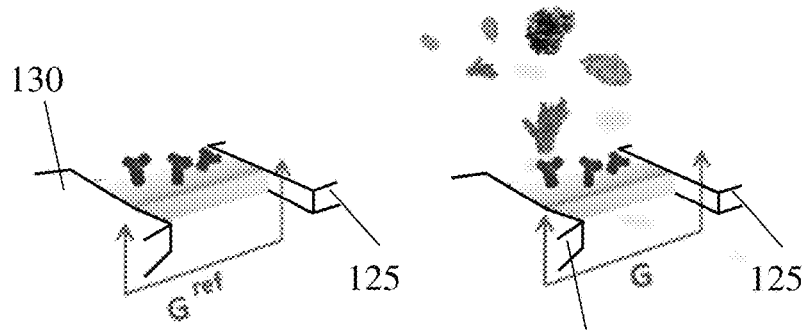
FIG. 1A  FIG. 1B  FIG. 1C
FIG. 1D  FIG. 1E

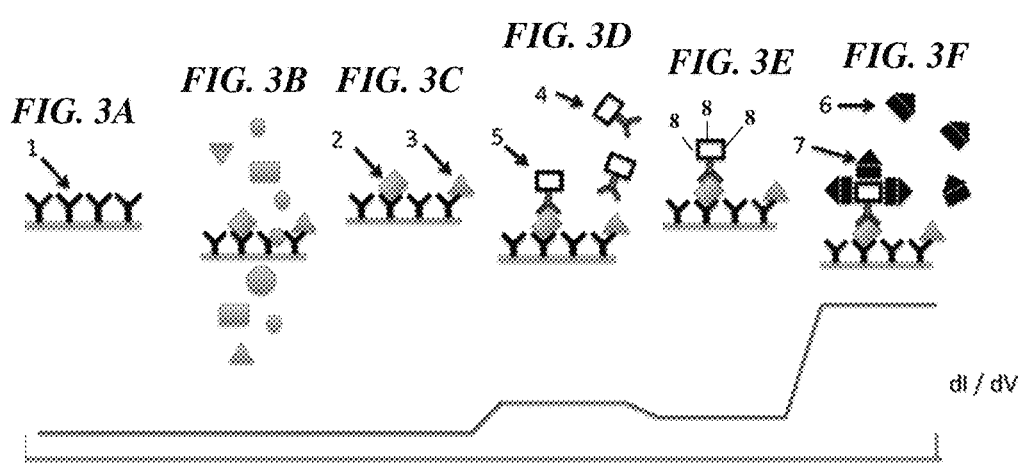

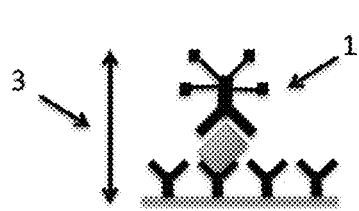
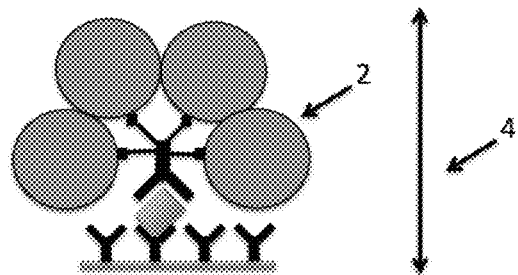
FIG. 6A  FIG. 6B

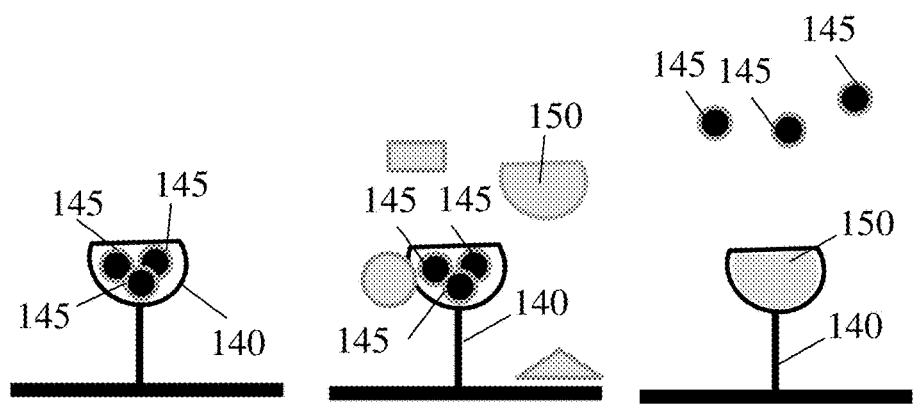
FIG. 7A  FIG. 7B  FIG. 7C
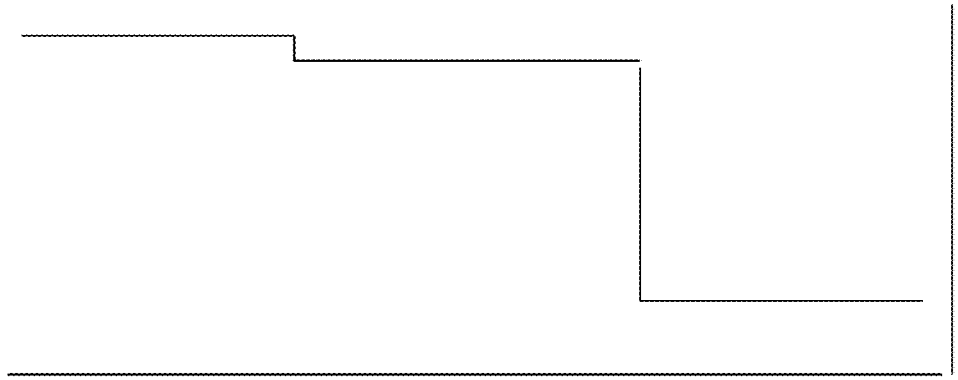

| Electrode | Electrode reaction | $E^{o}(V)$* | $E^{o'}(V)$† (pH 7) |
|---|---|---|---|
| $Li^+/Li$ | $Li^+ + e^- \rightarrow Li$ | -3.045 | |
| $K^+/K$ | $K^+ + e^- \rightarrow K$ | -2.925 | |
| $Cs^+/Cs$ | $Cs^+ + e^- \rightarrow Cs$ | -2.923 | |
| $Ca^{2+}/Ca$ | $Ca^{2+} + 2e^- \rightarrow Ca$ | -2.866 | |
| $Ca^+/Na$ | $Na^+ + e^- \rightarrow Na$ | -2.714 | |
| $Mg^{2+}/Mg$ | $Mg^{2+} + 2e^- \rightarrow Mg$ | -2.363 | |
| $OH^-/H_2/Pt$ | $2H_2O + 2e^- \rightarrow H_2 + 2OH^-$ | -0.8281 | |
| $Zn^+/ZN$ | $Zn^{2+} + 2e^- \rightarrow Zn$ | -0.7628 | |
| Acetate/acetaldehyde | $OAc^- + 3H^+ + 2e^- \rightarrow CH_3CHO + H_2O$ | | -0.58 |
| $Fe^{2+}/Fe$ | $Fe^{2+} + 2e^- \rightarrow Fe$ | -0.4402 | |
| Gluconate/glucose | $C_6H_{11}O_7^- + 3H^+ + 2e^- \rightarrow C_6H_{12}O_6 + H_2O$ | | 0.44 |
| Spinach ferredoxin | $Fe(III) + e^- \rightarrow Fe(II)$ | | -0.43 |
| $CO_2$/formate | $CO_2 + 2H^+ + 2e^- \rightarrow HCO_2^- + H^+$ | -0.20 | -0.42 |
| $NAD^+/NADH$‡ | $NAD^+ + H^+ + 2e^- \rightarrow NADH$ | -0.105 | -0.32 |
| $Fe^{3+}/Fe$ | $Fe^{3+} + 3e^- \rightarrow Fe$ | -0.036 | |
| $H^+/H_2/Pt$ | $2H^+ + 2e^- \rightarrow H_2$ | 0 | -0.421 |
| Mn hematoporphyrin IX | $Mn(III) + e^- \rightarrow Mn(II)$ | | -0.342 |
| Acetoacetate/β-hydrooxybutyrate | $CH_3COCH_2CO_2^- + 2H^+ + 2e^- \rightarrow CH_3CHOHCH_2CO_2^-$ | | -0.27 |
| Horseradish peroxidase | $Fe(III) + e^- \rightarrow Fe(II)$ | | -0.27 |
| Cytochrome c | $Fe(III) + e^- \rightarrow Fe(II)$ | | -0.25 |
| $FAD/FADH_2$§ | $FAD + 2H^+ + 2e^- \rightarrow FADH_2$ | | -0.22 |
| Acetaldehyde/ethanol | $CH_3CHO + 2H^+ + 2e^- \rightarrow CH_3CH_2OH$ | | -0.20 |
| Pyruvate/lactate | $CH_3COCO_2^- + 2H^+ + 2e^- \rightarrow CH_3CHOHCO_2^-$ | | -0.19 |
| Oxaloacetate/malate | $^-O_2CCOCH_2CO_2^- + 2H^+ + 2e^- \rightarrow ^-O_2CCHOHCH_2CO_2^-$ | | -0.17 |
| Fumarate/succinate | $^-O_2CCH=CHCO_2^- + 2H^+ + 2e^- \rightarrow ^-O_2CCH_2CH_2CO_2^-$ | | +0.031 |
| Myoglobin | $Fe(III) + e^- \rightarrow Fe(II)$ | +0.337 | +0.046 |
| $Cu^{2+}/Cu$ | $Cu^{2+} + 2e^- \rightarrow Cu$ | +0.5355 | |
| $I_2/I^-/Pt$ | $I_2 + 2e^- \rightarrow 2I^-$ | +0.69 | |
| $O_2/H_2O/Pt$ | $O_2 + 2H^+ + 2e^- \rightarrow H_2O_2$ | +0.771 | +0.295 |
| $Fe^{3+}/Fe^{2+}/Pt$ | $Fe^{3+} + 3e^- \rightarrow Fe^{2+}$ | | -0.25 |

*FIG. 8*

| Macromolecule | Size (kDa) | pI | Surface Dimension |
|---|---|---|---|
| Antibody | 150 kDa | 6.1 | 2-6 nm |
| Fab Antibody | 55 kDa | <4.5->9.3 | 2 |
| Fv | 28 kDa | <4.5->9.3 | 2 |
| Nanobody | 12 kDa | ? | <2 |
| Streptavidin | 52.8 kDa | ~5.6 | |
| Biotin | 244 Da | | assoc conjugate |
| Aptamer | ~10 kDa | | 2 |
| Nanocrystal-FeO | 4 nm | ** | assoc conjugate |
| Nanoparticle-Fe | >10 nm | ** | assoc conjugate |
| Nanoparticle-Au | 1 nm | ** | assoc conjugate |
| HRP VIII | 40 kDa | 3.6 | |
| HRP VI | | >10 | |
| Albumin | 67 kDa | 4.8 | nd |
| Transferrin | 80 kDa | 5.9 | nd |
| Lysozyme | 14.7 kDa | 11 | nd |

*FIG. 9A*

|  | Kd range | |
|---|---|---|
|  | HIGH | LOW |
| Antibody | micromolar | picomolar |
| Aptamer | micromolar | picomolar |
| RGD | nanomolar |  |
| Protein:Protein | micromolar |  |
| BCL2:BCLXL | nanomolar |  |
| AVIDIN:Biotin |  | 1.00E-14 |
| Nucleic acid |  |  |

*FIG. 9B*

| METAL | Form | Compound | Use |
|---|---|---|---|
| Fe | Fe(3)O(4)<br>Fe(2)O(3)<br>Mn<br>FeFe2O4<br>CoFe2O4<br>NiFe2O4 | MnFe2O4 | Nanoparticle<br>Nanocrystal<br>Doped-ferrite nanoparticles |
| Au | Au | | Nanoparticle |
| Ag | Ag/AgCl<br>Ag | | HRP |
| Pd | Pd | | Nanoparticle |
| Pt | Pt | | Thin Film/Nanoparticle |
| Ti | Ti | | Nanoparticle |

*FIG. 10*

METHODS FOR INCREASING THE MOLECULAR SPECIFICITY OF A NANOSENSOR

RELATED APPLICATIONS

This application claims priority under 35 U.S.C. § 119(e) to U.S. Provisional Patent Application Ser. No. 61/885,235, filed Oct. 1, 2013, and entitled "Methods for Increasing the Molecular Specificity of a Nanosensor," which is incorporated herein by reference in its entirety for all purposes.

TECHNICAL FIELD

Systems and methods for detecting a target species using a semiconductor nanosensor are generally described.

BACKGROUND

Silicon nanochannel field effect transistor (FET) nanosensors that utilize electrical detection mechanisms are a promising approach to the development of highly sensitive and label-free target species detection. Silicon nanochannels are well-suited for nanosensor applications due, in part, to the exceptional electrical properties and small dimensions. For instance, the small dimensions of silicon nanochannels allow them to have large surface to volume ratios that can result in relatively high electrical sensitivity. The relatively high electrical sensitivity allows silicon nanochannels to detect very low concentrations of the target species (e.g., a few molecules, a single molecule). FET nanosensors have numerous other benefits, such as high speed, low cost, and high yield manufacturing, amongst others, without sacrificing sensitivity. Moreover, top down manufacturing methods are able to leverage advantages in Complementary Metal Oxide Semiconductor technologies to make multiplexed FET nanosensor arrays.

Though FET nanosensors offer good sensitivity, specificity is a challenging issue. For example, the interaction of a target species with the detection element may be masked by less specific interactions of the detection element with other substances that have a greater abundance. Nanosensors must provide adequate sensitivity and specificity information to be used in applications such medical diagnostics, public health, epidemiologic studies, personalized medicine, monitoring, surveillance, agriculture, and defense industries. Accordingly, improved compositions and methods are needed.

SUMMARY

Systems and methods for detecting a target species using a semiconductor nanosensor are provided. The subject matter of the present invention involves, in some cases, interrelated products, alternative solutions to a particular problem, and/or a plurality of different uses of one or more systems and/or articles.

In one aspect, a system is provided. In some embodiments, the system comprises an amplification agent associated with a first species capable of participating in a molecular binding event and at least three binding agents and a second species capable of participating in a molecular binding event associated with the first species, wherein the second species is associated with a surface of a semiconductor nanosensor.

In one set of embodiments, a series of methods are provided. In some embodiments, the method comprises associating an amplification agent with a first species capable of participating in a molecular binding event that is associated with a surface of a semiconductor nanosensor, wherein the amplification agent is associated with at least three binding agents via binding sites on the amplification agent. After the associating step, the semiconductor nanosensor, in some embodiments, is capable of producing a signal-to-noise that is at least 2 times greater than a signal-to-noise ratio that would be produced in the absence of the associating step but under otherwise essentially identical conditions.

In certain embodiments, the method comprises associating at least three binding agents with at least three binding sites of an amplification agent capable of participating in a molecular binding event, wherein the amplification agent is associated with a surface of a semiconductor nanosensor. The semiconductor nanosensor, in some instances, is capable of producing a signal-to-noise ratio that is at least 2 times greater than a signal-to-noise ratio that would be produced in the absence of the associating step but under otherwise essentially identical conditions.

In some embodiments, the method comprises associating an amplification agent comprising binding sites with the first species capable of participating in a molecular binding event that is associated with a surface of a semiconductor nanosensor and associating at least three binding agents with at least three binding sites of the amplification agent. The semiconductor nanosensor, in certain embodiments, is capable of producing a first signal-to-noise ratio that is at least about 2 times greater than a signal-to-noise ratio that would be produced in the absence of the step of associating the at least three binding agents with at least three bonding sites of the amplification agent but under otherwise essentially identical conditions.

In one embodiment, the method comprises associating a first species with a second species such that the first and second species engage in a molecular binding event resulting in the release of agents from the first species or the second species, wherein the second species is associated with a surface of a semiconductor nanosensor. The semiconductor nanosensor, in certain embodiments, is capable of producing a signal-to-noise ratio that is at least 2 times greater than a signal-to-noise ratio that would be produced in the absence of the releasing step but under otherwise essentially identical conditions.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1A shows a schematic of a lithography step of the stepwise manufacturing of a FET device for diagnostic tests, according to certain embodiments;

FIG. 1B shows a schematic of a chemical treatment step of the stepwise manufacturing of a FET device for diagnostic tests, according to certain embodiments;

FIG. 1C shows a schematic of a functionalization with a species of the stepwise manufacturing of a FET device for diagnostic tests, according to certain embodiments;

FIG. 1D shows the measurement of a target species, according to certain embodiments;

FIG. 1E shows the measurement of a target species, according to certain embodiments;

FIG. 3A shows a schematic of a part of a diagnostic assay including an amplification agent and binding agents, according to certain embodiments;

FIG. 3B shows a schematic of a part of a diagnostic assay including an amplification agent and binding agents, according to certain embodiments;

FIG. 3C shows a schematic of a part of a diagnostic assay including an amplification agent and binding agents, according to certain embodiments;

FIG. 3D shows a schematic of a part of a diagnostic assay including an amplification agent and binding agents, according to certain embodiments;

FIG. 3E shows a schematic of a part of a diagnostic assay including an amplification agent and binding agents, according to certain embodiments;

FIG. 3F shows a schematic of a part of a diagnostic assay including an amplification agent and binding agents, according to certain embodiments;

FIG. 6A shows a schematic of the Debye length before association of binding agents with the amplification agent;

FIG. 6B shows a schematic of the Debye length after association of binding agents with the amplification agent;

FIG. 7A shows a schematic of a part of a diagnostic assay including releasing an agent, according to certain embodiments;

FIG. 7B shows a schematic of a part of a diagnostic assay including releasing an agent, according to certain embodiments;

FIG. 7C shows a schematic of a part of a diagnostic assay including releasing an agent, according to certain embodiments;

FIG. 8 shows a table of standard reduction potentials, according to certain embodiments;

FIG. 9A shows a table of macromolecules and factors that are considerations in their use in diagnostic assays, in some embodiments;

FIG. 9B shows exemplary species that may be bound to one or more surfaces of a semiconductor nanosensor, in some embodiments;

FIG. 10 shows a table of metals that may be used as binding agents, according to certain embodiments;

DETAILED DESCRIPTION

Figures 2A, 2B, 2C, 2D, 2E:
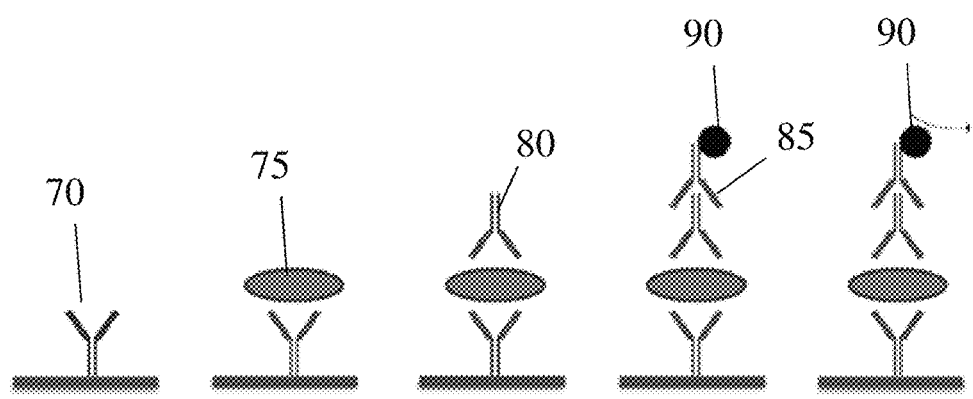
FIG. 2A shows a schematic of a part of a diagnostic assay including an amplification agent and binding agents, according to certain embodiments.
FIG. 2B shows a schematic of a part of a diagnostic assay including an amplification agent and binding agents, according to certain embodiments.
FIG. 2C shows a schematic of a part of a diagnostic assay including an amplification agent and binding agents, according to certain embodiments.
FIG. 2D shows a schematic of a part of a diagnostic assay including an amplification agent and binding agents, according to certain embodiments.
FIG. 2E shows a schematic of a part of a diagnostic assay including an amplification agent and binding agents, according to certain embodiments.

Systems and methods for detecting a target species using a semiconductor nanosensor are generally described. In some embodiments, a sensor system containing a semiconductor nanosensor, agents (e.g., amplification agent, binding agent), and species may be used for the electrical detection of a target species with relatively high specificity and sensitivity. In certain embodiments, a method for detecting the target species may utilize certain agents to increase the specificity and sensitivity of detection relative to conventional detection methods.

Many detection systems utilize one or more molecular binding events to detect and/or determine information (e.g., concentration, presence, absence) about a target species. As used herein, a molecular binding event may refer to a direct association between two or more molecules that occurs with high specificity and affinity. For example, the binding of an antigen to an antibody with a high specificity for the antigen is often used to detect the presence of the antigen in a sample (e.g., bodily fluid). However, electrical detection of a molecular binding event including the target species can be challenging in environments in which the concentration and/or relative abundance of the target species is low. Though techniques for optical amplification of a signal are well known, methods of amplifying an electrical signal to a molecular binding event are not. Some conventional electrical detection methods have tried to address this problem by utilizing additional, complex, costly, and/or time-consuming method steps and/or employing additional, large, and/or costly instrumentation. It has been unexpectedly discovered that relatively specific and sensitive detection of molecular binding events including a target species can be achieved using semiconductor nanosensors and agents (e.g., amplification agent, binding agents, releasable agents) that are capable of participating in a molecular binding event or associating with a target species and increasing the signal-to-noise ratio. These agents (e.g., amplification agent, binding agents, releasable agents) may be specific for the target species or molecules bound to the targets species and may serve to amplify the electrical signal associated with the molecular binding event involving the target species. In some embodiments, species that are configured to participate in a molecular binding event are selected based on their affinity and specificity for another agent or species, such as a target species. In some instances, it has been discovered that certain amplification agents used in optical detection may be modified as described herein for use in electrical amplification.

In some embodiments, a semiconductor nanosensor is used to detect and/or determine information about a target species with high specificity and sensitivity. The semiconductor nanosensor may comprise a field effect transistor comprising a source electrode and a drain electrode connected via a semiconductor nanochannel (e.g., a semiconductor nanowire, such as a silicon nanowire). In some such embodiments, at least a portion of one or more surfaces of the semiconductor nanochannel is functionalized with a species capable of participating or configured to participate in a molecular binding event with the target species or being indirectly associated with the target species. The functionalized surface(s) may serve as a molecular gate for the field effect transistor, such that alterations in the electrical field caused by a molecular binding events affects the electrical signal (e.g., current) received at the drain electrode. In some embodiments, the semiconductor nanosensors may be configured to monitor the capacitance, voltage, or conductance attributable to a target species.

A non-limiting example of a semiconductor nano sensor comprising a field effect transistor that may be used to detect a target species and an exemplary method of fabricating the FET is shown in FIGS. 1A-E. In some embodiments, a field effect transistor 100 may be formed by lithography, as shown in FIG. 1A, to produce a nanochannel having a dimensionality and surface area that maximizes or greatly enhances the nanochannel's sensitivity to changes in electric field, due for example, to changes in surface charge. For example, as illustrated in FIG. 1B, nanochannel 110 can be formed by etching a semiconductor substrate such that a nanowire is formed. In some embodiments, the nanochannel can be undercut (e.g., using an appropriate etchant) to form a freestanding nanochannel. In some embodiments, electrodes 125 and 130 can be formed adjacent the nanochannel. Electrodes 125 and 130 can function as the drain and source electrodes as part of a FET sensor, as described in more detail below.

After an optional treatment (e.g., chemical treatment), in certain embodiments, at least a portion of one or more surfaces of the semiconductor nanosensor (e.g., one or more nanochannel surfaces) may be functionalized, such that a species can be bound, directly or indirectly, to at least a portion of a surface of the semiconductor nanosensor. For instance, as shown in FIG. 1B, one or more surfaces of the nanochannel 110 may be functionalized with a bound species to form the molecular gate. Bound species may be a biological or chemical species capable of participating or configured to participate in a molecular binding event or associated with the target species. In certain embodiments, the bound species may be a nucleic acid (e.g., DNA, RNA, aptamer), a peptide, a protein (e.g., antibody), receptor molecule, polymer, supramolecular structure, or small molecule that can participate in a specific molecular binding event with the target species (e.g., an antibody, aptamer, receptor molecule, peptide, protein, nucleic acid, gene, small molecule) or a species associated with the target species. For instance, as shown in FIG. 1C, the bound species may be antibodies 120 that are bound, directly or indirectly, via a covalent or non-covalent bond to a surface of nanochannel 110.

In the absence of any non-specific or specific associations between a biological and/or chemical molecule and bound species and/or the surface of the nanochannel, the nanochannel experiences a first electric field which produces a first electrical signal that serves as the reference or background electrical signal, as shown in FIG. 1D. For example, in the absence of a sample, the drain electrode 125 may receive a first current from the source electrode 130 due to the first conductance of nanochannel 110. When the semiconductor nanosensor is brought in contact with a sample, such as a heterogeneous mixtures of disease-relevant proteins in, e.g., blood, saliva, or another fluids, any non-specific or specific associations between a biological and/or chemical molecule and bound species and/or the surface of the nanochannel will cause the FET to experience a second signal which produces a second electrical signal as shown in FIG. 1E. The change in the signal indicates associations have occurred. Non-limiting examples of samples include an antibody-containing solution such as blood, serum, synovial fluid, cerebrospinal fluid, sputum, tumor lysates, ascites, and the like, that is being examined for the purpose of detection and quantitation.

As noted above, in embodiments in which non-specific associations occur, it may difficult to distinguish between non-specific associations and molecular binding events involving the target species, especially when the magnitude of the electrical signal is dependent on the concentration of the target species. For instance, a relatively low concentration of a target species in a sample may produce a change in the electrical field that is relatively small compared to the change in the electrical field produced by non-specific association. In such cases, the non-specific associations may mask the presence of the target species. However, when the concentration of the target species is relatively high, the magnitude of the change in the electric field due to molecular binding events with the target species is significantly higher than non-specific association and can be easily distinguished. Accordingly, in certain embodiments, the limit of detection of a target species in a sample may be limited by the magnitude of the electrical signal produced from molecular binding events involving the target species relative to the magnitude of the electrical signal not associated with a molecular binding event involving the target species (e.g., non-specific association).

The ratio between the magnitude of electrical signal produced by the nanosensor from molecular binding events involving the target species and the magnitude of the electrical signal produced by the nanosensor due to all factors other than the molecular binding events may be referred to as the signal-to-noise ratio. The signal-to-noise ratio may be determined by measuring the electrical signal before and after addition of a sample to a nanosensor functionalized with a bound species specific for the target species in the sample. In some instances, the electrical signal before and after addition of the sample to a nanosensor that is not functionalized or not functionalized with a bound species specific for the target species in the sample is subtracted to provide the signal-to-noise ratio. Thus, in some such embodiments, association between the species bound (directly or indirectly) to the nanosensor and the target species may produce an electrical signal with a certain signal-to-noise ratio. The signal-to-noise ratio may limit the specificity and sensitivity of detection. A low signal-to-noise ratio can adversely affect the limit of detection, such that a low concentration or abundance of the target species may not be able to be accurately detected. In some embodiments, the detection of the presence, absence, and/or concentration of certain target species may require the electrical signal associated with molecular binding events involving the target species to be amplified.

In some embodiments, the magnitude of the electrical signal associated with molecular binding events involving the target species may be significantly amplified using certain agents that have a high specificity for the target species or species associated with the target species. In some embodiments, these agents (e.g., amplification agent, binding agents, releasable agents) may significantly increase both the sensitivity and specificity of the assay. In general, any agent capable of specifically associating or configured to specifically associate with the target species and capable of perceptively altering the electrical field when associated, directly or indirectly, with the target species may be used to increase the signal-to-noise ratio. In some embodiments, a suitable amplification agent may increase the surface potential of the nanochannel by more than 25 mV. In certain embodiments, the association between the binding agent and the amplification must have a high enough association constant to withstand one or more washing, fluid addition, or fluid removal steps without dissociating. In some embodiments, suitable releasable agent(s) may cause a change in the surface potential of at least about 50 mV. In embodiments in which more than one releasable agent is used, change in the surface potential due to all the released agents may be at least about 50 mV. In general, the charge content and distribution may be a major contributing factor toward an electrical signal on a nanosensor. In some embodiments, macromolecular components that are linked by chemistry, conjugation, and/or molecular binding processes contribute to the overall charge properties of the surface of the semiconductor nanosensor. Non-limiting examples of assays on a semiconductor nanosensor that includes one or more agents to amplify the magnitude of the electrical signal due to molecular binding events involving the target species is shown in FIGS. 2-5.

FIG. 3 shows a schematic of exemplary procedure for an assay performed on a FET of a semiconductor nanosensor that utilizes one or more agents to amplify the desired electrical signal. In some embodiments, the assay may begin by activating the semiconductor nanosensor comprising a FET having a nanochannel functionalized with bound species 1 (e.g., antibody), shown in FIG. 3A, that is capable of undergoing a molecular binding event with the target species (e.g., antigen). In certain embodiments, the activation may comprise the removal of stabilizing agents and hydration of the surface. In other embodiments, an activation agent is not required prior to loading a sample. As illustrated in FIG. 3B, a sample is added to the activated nanosensor. In general, the sample may be in any suitable form that allows for diffusion of the target species to and association with a species bound, directly or indirectly, to the nanochannel. The sample may be introduced to the nanochannel using any suitable technique, including the use of microfluidics and various forms of sample injection as applicable for research, clinical, and point-of-care devices. In certain embodiments, the sample is incubated with the nanochannel for a given period of time, which is dependent on the binding kinetics of the molecular binding event and the composition of the sample.

As illustrated in FIG. 3C, the sample may be removed from the semiconductor nanosensor such that only the target species 2 and species 3 that is non-specifically associated with the nanochannel and/or bound species 1 remain. The change in the electrical field as a result of the association of species 2 and 3 may cause a change in the electrical field around the nanochannel. In certain embodiments, as illustrated in FIG. 3C, the magnitude of the change may be relatively small such that a change in electrical signal is not detected. In some embodiments, an amplification agent may be used to increase the magnitude of the change associated with the molecular binding event involving the target species. As illustrated in FIG. 3D, an amplification agent 4 that is capable of or configured to undergoing a molecular binding event with the target species associated with bound species 1 may be added. The amplification agent may be a biological or chemical agent (e.g., antibody, enzyme, supramolecular structure, nanoparticle) that is capable of participating in a molecular binding event. Amplification agent 4 may undergo a molecular binding event with species 2 to form complex 5. Formation of complex 5 may further change the electric field within a Debye length of the nanochannel and result in a detectable change in the electrical signal as shown in FIGS. 3D and 3E.

In some embodiments, the change resulting from the formation of complex 5 may not be sufficient to accurately determine the presence, absence, and/or concentration of the target species. In some such embodiments, the amplification agent may comprise a plurality of binding sites 8 (e.g., at least three binding sites), shown in FIG. 3E, that can be associated with binding agents capable of or configured to further amplifying the electrical signal associated with the molecular binding event. As illustrated in FIG. 3F, the molecular binding event between the binding agents 6 and the amplification agent 4 associated with the target species may lead to the formation of complex 7, which significantly increases the electrical signal attributable to the target species and the signal-to-noise ratio. In some embodiments, the binding agent may be a small molecule, a particle, or a biological macromolecule. For instances, in certain embodiments, a small molecule may be used as the binding agent in the procedure shown in FIGS. 3A-E. In some such embodiments, the amplification agent is a protein comprising SET and ring finger associated protein domains (SRA) and a recognition site for the target species. The protein binds to the target species and also has binding sites for adenosine monophosphate (AMP), which acts as the binding agent. AMP is highly negatively charged and binding of multiple AMPs to the protein significantly changes the electric field around the nanochannel.

Figure 5A:
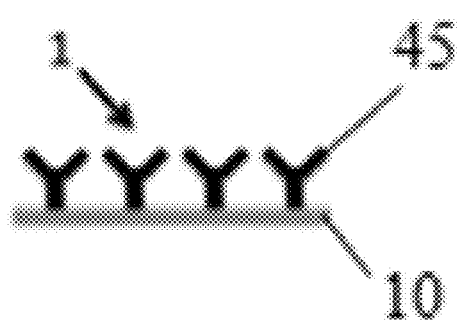
FIG. 5A shows a schematic of a part of a diagnostic assay including an amplification agent and binding agents, according to certain embodiments.
Figure 5B:
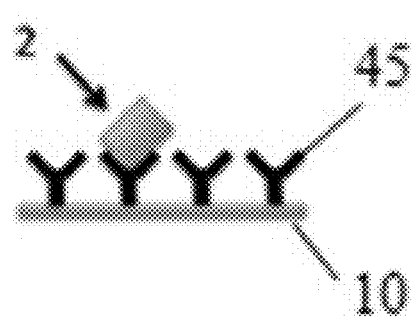
FIG. 5B shows a schematic of a part of a diagnostic assay including an amplification agent and binding agents, according to certain embodiments.

As illustrated in FIGS. 5A-D, in some embodiments, nanoparticles may be used as binding agents to increase the signal-to-noise ratio. In some embodiments, a semiconductor nanosensor may comprise a nanochannel 10 having one or more surfaces functionalized with a bound species 45 as illustrated in FIG. 5A. In some instances, bound species 45 (e.g., antibody) may be directly bond to one or more surfaces, of the semiconductor nanosensor, e.g., via covalent bond. The bound species may have a relatively high specificity for the target species 2 and readily associated with target species upon addition of the sample as shown in FIG. 5B. In embodiments in which the molecular binding event between the bound species and target species does not have a sufficient signal-to-noise ratio, an amplification agent may be associated, directly or indirectly, with the target species.

Figure 5C:
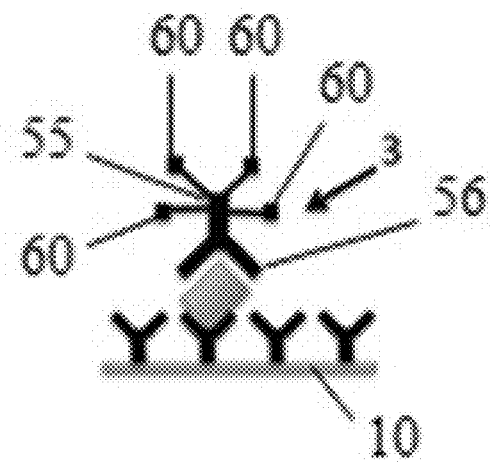
FIG. 5C shows a schematic of a part of a diagnostic assay including an amplification agent and binding agents, according to certain embodiments.
Figure 5D:
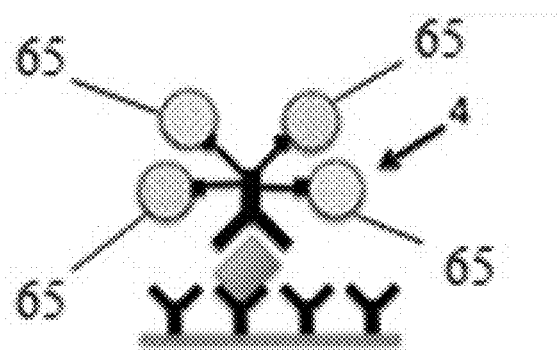
FIG. 5D shows a schematic of a part of a diagnostic assay including an amplification agent and binding agents, according to certain embodiments.

In some instances, as illustrated in FIG. 5C, an amplification agent 55 is directly associated with a target species 50 that is associated with bound species 45. In other instances, the amplification agent may be indirectly associated with the target species via another species that is directly associated with the target species via a molecular binding event. As illustrated in FIG. 5D, a plurality of binding agents 65 may be associated with a least a portion of the binding sites 60 on the amplification agent 55. In certain embodiments, the binding agents, in conjunction with amplification agent, may significantly increase the electrical signal, and accordingly the signal-to-noise ratio, attributable to a molecular binding event involving the target species. In certain embodiments, as illustrated in FIG. 5D, the binding agents may be nanoparticles. In some such embodiments, amplification agent may be an antibody with nanoparticle binding sites. The amplification agent 55 may have a region 56 that binds to a target species 50 and binding sites 60 that bind to nanoparticles. In some instances the nanoparticles in conjunction with the amplification agent may be used to increase the electrical signal, e.g., conductance, within a Debye length of the nanosensor surface and thereby increase the signal-to-noise ratio of the molecular binding event involving the target species.

Figures 4A, 4B, 4C, 4D:
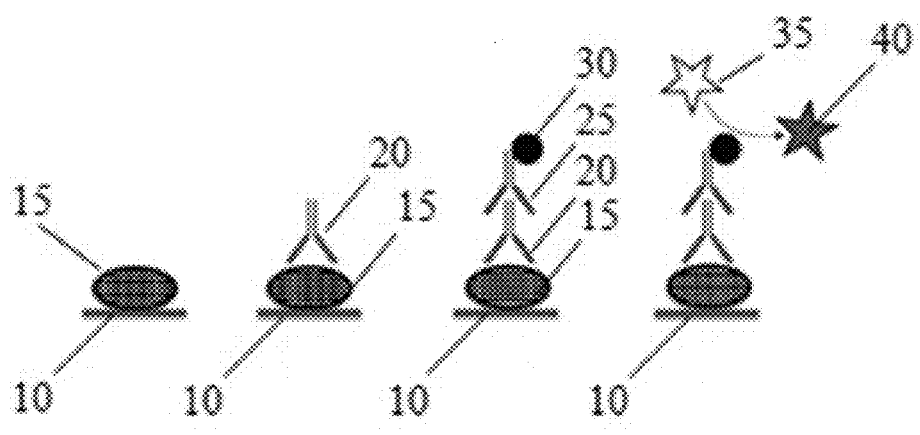
FIG. 4A shows a schematic of a part of a diagnostic assay including an amplification agent and binding agents, according to certain embodiments.
FIG. 4B shows a schematic of a part of a diagnostic assay including an amplification agent and binding agents, according to certain embodiments.
FIG. 4C shows a schematic of a part of a diagnostic assay including an amplification agent and binding agents, according to certain embodiments.
FIG. 4D shows a schematic of a part of a diagnostic assay including an amplification agent and binding agents, according to certain embodiments.

In some embodiments, the assay performed on the semiconductor nanosensor may be an enzyme-linked immunosorbent assay (ELISA) as shown in FIGS. 2 and 4. In some such embodiments, the enzyme may act as the amplification agent and the reaction products of the enzyme may act as binding agents. For instance, as illustrated in FIGS. 4A-D, the assay may be an indirect ELISA. As illustrated in FIG. 4, at least a portion of the surface of nanosensor 10 may be functionalized, such that a bound species 15 capable of participating or configured to participate in a molecular binding event with the target species is bound, directly or indirectly, to the surface of the semiconductor nanosensor. During operation of the semiconductor nanosensor, the species 15 bound to the surface is exposed to a sample (e.g., bodily fluid, water). In some instances, the sample contains the target species 20. The target species may have a relatively high specificity and/or affinity for bound species 15, such that bound species 15 undergoes a molecular binding event with the target species. In some instances, as illustrated in FIG. 4, the bound species is an antigen and the target species is an antibody. As illustrated in FIG. 4C, the amplification agent 25 may bind to the target species with relatively high specificity and/or affinity. In some embodiments, the amplification agent may comprise an enzyme 30 having non-specific or specific binding sites for binding agents. For example, as illustrated in FIGS. 4C-D, the amplification agent may be an antibody conjugated to an enzyme. The antibody portion may bind to the target antigen with high specificity and affinity. The enzyme portion may convert a substrate 35 to a reaction product 40 and the enzyme may have non-specific or specific binding sites for the reaction product, such that at least a portion of the reactant product associates with the enzyme portion. In some such embodiments, the substrate may be selected based on redox potential of the enzymatic reaction as well as the electrical properties of the resulting reaction product and its ability to associate with the enzyme. For instance, substrates that produce a relatively large redox potential may be used. The reaction product in conjunction with the enzyme may be used to amplify the electrical signal associated with the target species and increase the signal-to-noise ratio thereby increasing the sensitivity and specificity of detection. In some embodiments, the complex formed on the surface of the semiconductor nanosensor by the species (e.g., target species and species bound to the nanosensor) and agents (e.g., amplification agent and binding agents) are within a Debye length of the nanosensor.

In some embodiments, the assay is a sandwich ELISA, as shown in FIGS. 2A-E. As illustrated in FIGS. 2A-B, a species 70 bound to the semiconductor nanosensor may undergo a molecular binding event with the target species 75 upon addition of a sample containing the target species. To further enhance specificity, a species 80 having a high specificity for target species may be added and readily bind with the target species as shown in FIG. 2C. The amplification agent 85 may have a high specificity for species 80 and undergo a molecular binding event with species 80 and thus become indirectly bound to the target species as shown in FIG. 2D. As illustrated in FIG. 2E, an enzyme 90 may be bound to the amplification and used to increase the electrical signal, and accordingly the signal-to-noise ratio, attributable to the molecular binding event involving the target species as described above with respect to FIG. 4.

Another non-limiting example of an assay that utilizes one or more agents to amplify the desired electrical signal is shown in FIGS. 7A-C. In some embodiments in which the molecular binding event between the target species and the species bound, directly or indirectly, to a portion of the surface of the semiconductor nanosensor is not be sufficient to accurately determine the presence, absence, and/or concentration of the target species, a releasable agent may be used to amplify the electrical signal and accordingly the signal-to-noise ratio attributable to the molecular binding event involving the target species. For instance, in some embodiments, a bound species 140 having a high specificity for a target species may be bound to a portion of a surface of a semiconductor nanosensor (e.g., a surface of a nanochannel) as shown in FIG. 7A. The species 140 may be associated with releasable agents 145. In some embodiments, the releasable agents may be associated with species 140 via a non-specific non-covalent interaction (e.g., electrostatic interaction, van der Waals interaction) and have a relatively low or specificity for bound species 140. In certain embodiments, the releasable agents may be associated with bound species 140 via a specific interaction that has a lower affinity for bound species 140 than the target species. Regardless of whether the association between the releasable species 145 and bound species 140 is specific or non-specific, the target species is capable of readily disassociating the releasable species 145 from bound species 140. For instance, as illustrated in FIGS. 7B-C, upon addition of the sample, the target species 150 may associate with bound species 140 causing releasable agents 145 to disassociate from bound species 140. It should be understood that though FIG. 7 depicts a plurality of releasable agents, in some instances, a single releasable agent may be used.

In some embodiments, as illustrated in FIG. 7A, the association between the releasable agents and bound species 140 may result in an electrical signal with a relatively large magnitude. In some instances, non-specific binding of components in the sample and the species and/or a portion of the surface of the semiconductor nanosensor may cause the electrical signal to increase slightly. In other instances, the electrical signal may decrease slightly as a result of the displacement of one or more releasable agents due to binding of certain sample components. The molecular binding event between the target species 150 and bound species 140 may cause a relatively large percentage (e.g., greater than or equal to about 50%, greater than or equal to about 60%, greater than or equal to about 70%, greater than or equal to about 80%, greater than or equal to about 90%, greater than or equal to about 95%, greater than or equal to about 98%) or all of the releasable agent to disassociate from the bound species. After disassociation, the releasable agents may not be within a Debye length of the semiconductor nanosensor and may not be electrically detectable. In some embodiments, the disassociation of the releasable agents from the bound species causes a significant decrease in the electrical signal as shown in FIG. 7C. The decrease in the electrical signal acts to increase the signal-to-noise ratio of the molecular binding event by greatly reducing the noise.

It should be understood that though the methods illustrated in the Figures depict a certain order of steps, the steps of the method may occur in any suitable order. For example, the bound species may be associated with the releasable agents prior to first use of the semiconductor nanosensor or immediately before introduction of the sample. As another example, the amplification agent may associate with binding agents prior to associating with the target species and/or a species associated with the surface of the semiconductor nanosensor. In some cases, the amplification agent may associate with the target species or species associated with the target species prior to becoming associated with, indirectly or directly, the surface of the semiconductor nanosensor. For instance, in some embodiments, a method for detection comprises associating an amplification agent with a first species capable of participating or configured to participate in a molecular binding event that is associated with a surface of a semiconductor nanosensor. In some such embodiments, the amplification agent may be associated with a plurality of binding agents (e.g., at least three) via binding sites on the amplification agent. After the associating step, the semiconductor nanosensor may be capable of producing a signal-to-noise ratio that is at least 2 times greater than a signal-to-noise ratio that would be produced in the absence of the associating step but under otherwise essentially identical conditions.

In some embodiments, a method for detection comprises associating a plurality of binding agents (e.g., at least three) with a plurality of binding sites (e.g., at least three) of an amplification agent that is associated with a surface of a semiconductor nanosensor. In some such cases, the semiconductor nanosensor is capable of or configured to producing a signal-to-noise ratio that is at least 2 times greater than a signal-to-noise ratio that would be produced in the absence of the associating step but under otherwise essentially identical conditions.

In some embodiments, a method for detection comprises associating a first species with a second species such that the first and second species engage in a molecular binding event resulting in the release of agents from the first species or the second species. In some such cases, the second species is associated with a surface of a semiconductor nanosensor and the semiconductor nanosensor may be capable of or configured to producing a signal-to-noise ratio that is at least 2 times greater than a signal-to-noise ratio that would be produced in the absence of the releasing step but under otherwise essentially identical conditions.

As described herein, after an associating or releasing step, the semiconductor nanosensor may be capable of producing a signal-to-noise ratio that is at least 2 times greater (e.g., at least 5 times greater, at least 10 times greater, at least 20 times greater, at least 50 times greater, at least 100 times greater) than a signal-to-noise ratio that would be produced in the absence of the associating step but under otherwise essentially identical conditions. In some instances, the magnitude of the improvement in the signal-to-noise ratio is between about 2 and about a 1 billion, between about 2 and about 1 million, between about 2 and about 100,000, between about 2 and 10,000, between about 5 and 1,000, or between about 10 and 1,000.

In some embodiments, the associating step may be any association that causes the amplification agent and binding agents to be bound, directly or indirectly, to the surface of the semiconductor nanosensor. In certain embodiments, the releasing step may be any association that causes an agent with electrical properties to become unbound, directly or indirectly, from the surface of the semiconductor nanosensor.

As described herein, a method for detecting and/or determining information about a target species utilizing a semiconductor nanosensor may employ certain agents to further increase specificity and sensitivity. As mentioned above, an amplification agent may be used to increase the specificity and sensitivity of detection. In general, the amplification agent may be any suitable molecule that is capable of participating or configured to participate in a molecular binding event that is associated with a target species, has binding sites for binding agents, and is capable of increasing or configured to increase the electrical signal and/or signal-to-noise ratio associated with a molecular binding event involving the target species. Non-limiting examples of amplification agents include an antibody conjugated to enzyme (e.g., antibody conjugated to horseradish peroxidase), an antibody with a plurality of binding sites (e.g., antibody with nanoparticles binding sites, antibody with metal binding sites), an antibody engineered to host secondary antibodies, an antibody engineered to contain specific charge states, an antibody containing at least one protein domains, an antibody conjugated to a DNA, an antibody conjugated to a peptide, an antibody containing an aptamer, or antibody conjugated to an aptamer. According to certain embodiments, the amplification agent comprises a plurality of binding sites. For instance, in some embodiments, the amplification agent may have at least 3 binding sites, at least 4 binding sites, at least 6 binding sites, at least 8 binding sites, at least 10 binding sites, at least 15 binding sites, or at least 20 binding sites (and/or, in certain embodiments, up to 100 binding sites, or more). The binding sites may have a high specificity and affinity for certain binding agents.

In some embodiments, the amplification agent may be an enzyme (e.g., alkaline phosphatase, lactoperoxidase, beta-galactosidase, heme proteins). The enzyme may be tethered to any species capable of or configured to undergoing a molecule binding event with a target species, such as antibodies, aptamers, or nucleic acids. For example, the amplification agent may be horseradish peroxidase (HRP) that is tethered to an antibody such that HRP retains its enzymatic activity and is within a Debye length of the semiconductor nanosensor. In some such embodiments, the HRP substrates are selected such that the HRP enzymatic conversion of the substrate leads to a change in redox potential and the reaction product remains associated with the, but not in the enzymatic pocket, of the HRP, which is tethered to the nanosensor by means of the antibody conjugation. Though HRP enzymatic reaction is only capatible with specific hydrogen acceptors, a wide variety of hydrogen donors may be used. Accordingly, the hydrogen donor may be selected based on its ability to increase the electrical signal associated with the enzymatic reaction and based the ability of the reaction product to associate with the enzyme. Non-limiting examples of suitable hydrogen donors include a large number of phenols (e.g., 4-chloronaphthol), aminophenols, diamines (e.g., diaminobenzidine), indophenols, leuco dyes, ascorbate, and several amino acids can react as a hydrogen donor. By utilizing this strategy, a fixed large voltage can be assembled in proximity to the sensor surface. As a result, strong electrical properties can be associated with the binding of the target species.

The table in FIG. 8 includes standard reduction potentials ($E°$ and $E°'$) for metals, small ligands, biochemical reactions, proteins for enzymatic reactions which can be used in with certain embodiments. Electron addition can lead to a significant reduction potential change as illustrated. The magnitude of these changes is transferrable to nanosensor surfaces with these or other molecules on the surface, according to certain embodiments. Note that, in the table shown in FIG. 8, reduction potentials are listed in Volts (V).

In some embodiments, as described herein, the amplification agent may be indirectly associated with the target species. In some such embodiments, the amplification agent has a high specificity for the species or a portion of the species that binds the target species. For example, a biotin molecule may be tethered to the species that binds the target species. The amplification agent may associate with the species directly bound to target species via an avidin moiety tethered to the amplification agent. In another example, the amplification agent may comprise an antibody that has a high specificity for the species directly bound to the target species. Non-limiting examples of molecules that can bind with the amplification agent or may be modified to bind with the amplification agent include antibodies, aptamers, avidin, and other macromolecules.

In some embodiments, as described herein, binding agents may be used to increase the signal-to-noise ratio. In general, any binding agent capable of associating or configured to associate with the binding sites of the amplification agent and increasing the signal-to-noise ratio may be used. In some embodiments, a significant portion of the increase in the signal-to-noise ratio may be due to the electronic properties of the binding agent. Non-limiting examples include metals, metal nanoparticles, small molecules (e.g., glucose, ammonia, hydrogen peroxide), heme proteins, certain amino acids motifs (e.g., polyhistidine tags), polymeric nanoparticles, quantum dots, silica-coated quantum dots, oxide coated quantum dots, multi-layer dielectric coated quantum dots, and dendrimers (e.g., biodendrimers). In some embodiments, a threshold number of binding agents (e.g., at least three binding agents) may associate with the amplification agent to produce a desired increase in the signal-to-noise ratio. In some embodiments, the relative increase in the signal-to-noise ratio is related to the number of binding agents associated with the binding sites. For instance, the signal-to-noise ratio may increase as the number of binding agents associated with the amplification agent increases. In some embodiments, the amplification agent may be associated with at least 3 binding agents, at least 4 binding agents, at least 6 binding agents, at least 8 binding agents, at least 10 binding agents, at least 15 binding agents, or at least 20 binding agents (and/or, in certain embodiments, up to 100 binding agents, or more).

In some embodiments, the binding agent may be bound to the amplification agent prior to its utilization in the assay. For example, the amplification may be an antibody tethered to a plurality of nanoparticles. In other embodiments, the binding agent may be bound to the amplification agent during the assay. In some embodiments, the amplification agent may have a natural binding site for the binding agents. In other embodiments, the amplification may have a synthetic binding site for the binding agents. For instance, in some embodiments, the amplification may be modified to possess a functional group or molecule that allows the amplification agent to bind with the binding agent. For example, the amplification agent may comprise a plurality of biotin molecules and the binding agents may comprise avidin or streptavidin attached to the species described herein as suitable binding agents. In certain embodiments, the binding agent may be covalently linked to the amplification agent using appropriate conjugation chemistry. For instance, cycloaddition reactions such as between a trans-cyclooctene (TCO) modified antibody and a tetrazine (Tz) modified nanoparticle may occur. In some embodiments, the molecular binding event between the amplification agent and the binding agent may contribute to the increase in the signal-to-noise ratio.

In certain embodiments, the binding agents may be nanoparticles comprising metals, metal oxides, and/or salts. Exemplary nanoparticles that may be utilized in the device include, but are not limited to, one or more metals, metal oxides, salts, or other inorganic or organic materials or composites thereof. Non-limiting examples of metals include Mg, Al, Ti, V, Cr, Mn, Fe, Co, Ni, Zn, Mo, Rh, Pd, Sn, W, Pt, Pb, Au, Cu, Ir, Ru, Os, Ag, combinations thereof and the like. The table in FIG. 10 indicates a group of metals that may be included in nanoparticles that will confer electrical properties, according to some embodiments.

In some embodiments, the nanoparticles may be in the form of nanocrystals. Metal nanocrystals have electronic properties differing greatly from their bulk counterparts. Examples of such metals include platinum, palladium, gold, nickel, cobalt, and manganese, amongst others. In certain embodiments, the nanocrystals are coated with organic monolayers to control their solubility in solvents. In addition, these layers may be an attachment matrix for molecular recognition properties. In some embodiments, nanocrystals having nanometer scale dimensions (e.g., 1-20 nm) are used. In particular, homogeneous nanocrystals of about 4 nm can be used, according to certain embodiments. Also, nanocrystals that are streptavidin coated and having a size of about 4 nm may be used, according to some embodiments. In some embodiments, nanoparticles may also be composed of multiple nanocrystals due to defects, twinning, and other known effects. Nanoparticles of metals may be composed of essentially a single nanocrystal domain with surface states, in some cases, or of multiple nanocrystals, and with substantial amorphous content. According to certain embodiments, a number of metals may be used in nanoparticles, nanocrystals, and the like.

Non-limiting examples of methods of modifying particles to be suitable binding agents for an amplification agent include the use of Streptavidin-conjugated nanoparticles (e.g., streptavidin-iron oxide nanoparticles; streptavidin-Au nanoparticles; streptavidin-Ag nanoparticles) to bind to an amplification agent having biotin groups. Alternatively the nanoparticles may have biotin and the amplification agent may comprise streptavidin. In some embodiments, the particles (e.g., nanogold) are attached to the amplification agent, either before or during the assay, using covalent bond forming methods, such as mono-amino, mono-maleimide, or mono-succinimide chemistry. In some instances, the particles may bind to the amplification agent via non-covalent bonds, such as electrostatic interactions.

Another example of a class of molecules with electrical properties that can be used as binding agents is electret particles. As used herein, electret may refer to a dielectric material that has a quasi-permanent electric charge or dipole polarization. An electret can generate internal and external electric fields, and can be thought of as the electrostatic equivalent of a permanent magnet. Electrets can also be manufactured by embedding excess negative charge within a dielectric using barium, strontium, titanate, cadmium sulfate, and related ferroelectric materials, prepared in the form of small particles.

As mentioned above, releasable agents may be used to increase the sensitivity and specificity of detection. In general, the releasable agents may be any suitable molecule or nanoparticle that is capable of being or configured to be released from a species due to a molecular binding event between that species and the target species and is capable of altering or configured to alter the electrical signal and/or increasing the signal-to-noise ratio associated with a molecular binding event. In general, the releasable agent will have a lower affinity for the species than the target species. Non-limiting examples of releasable agents include small molecules (e.g., hydrogen peroxide, ionic compounds, non-fluorescent small molecules, metal complexes), ions (e.g., hydrogen ion), protein domains, nanoparticle, and fluorescent tags. In general, a range of release techniques may be used that can distinguish molecules based on one or more physical, chemical, electrical or optical differences among molecules being released including but not limited to molecular weight, shape, solubility, pKa, hydrophobicity, charge, charge/mass ratio, polarity, electrophoretic mobility, etc.

In some embodiments, a threshold number of releasable agents (e.g., at least three agents) are released from a species associated with semiconductor nanosensor to produce an increase in the signal-to-noise ratio. In some embodiments, the relative increase in the signal-to-noise ratio is related to the number of agents released from the bound species associated with semiconductor nanosensor. For instance, the signal-to-noise ratio may increase as the number of agents released increases. In some embodiments, at least 3 agents, at least 4 agents, at least 6 agents, at least 10 agents, at least 25 agents, at least 50 agents, or at least 100 agents (and/or, in certain embodiments, up to 500 agents, or more) may be released from a species associated with the semiconductor nanosensor (e.g., a species directly associated with the surface of the semiconductor nanosensor, a species indirectly associated with the surface of the semiconductor nanosensor).

In some embodiments, the releasable agent may be associated with the species bound, directly or indirectly, to a portion of the surface of the semiconductor nanosensor via a noncovalent interaction. In some such embodiments, the releasable agent may be electrostatically bound to the species and may confer electrical properties. The releasable agent may be pre-loaded or pre-charged as part of the manufacturing process of the functionalized nanosensor. In one example, $[Ru(NH_3)_6]^{3+}$ cations may be added to an aptamer bound to the nanosensor surface. The aptamer may have thrombin recognition properties, such that the aptamer has a higher affinity for thrombin than $[Ru(NH_3)_6]^{3+}$ cations. Binding of thrombin to the aptamer can be used to confer a release of the $[Ru(NH_3)_6]^{3+}$ into the aqueous solution, and loss of association with the tethered complex. In some such embodiments, the electrical impact is thus to change the overall conductance of the tethered aptamer surface potential, and impacts both the polarity and the magnitude of the conductance differential.

In some embodiments, a semiconductor nanosensor system and/or method utilizing a semiconductor nanosensor may be configured to detect and/or determine information about a specific species (i.e., target species). In general, the target species may be any molecule of diagnostic value. For instance, in some embodiments, the target species may be a nucleic acid, a biomarker, a gene, a protein, a peptide, supramolecular structure, nanoparticle, a small molecule (e.g., therapeutics, toxin, metal, metabolite, cofactor, metal containing compound, ligand) macromolecule, receptor, biological cell, biological cell cluster, single-cell organism, virus, or a multi-cellular organism.

In some embodiments, a method for detecting a species (e.g., a target species) may comprise associating species and/or agent(s) with each other. In general, any suitable method may be used to bring a species and/or agent together, such that association occurs. Those of ordinary skill in the art would be knowledgeable of methods of bringing a species and/or agent together to cause association. In general, the association between species and/or agents can be of any suitable type. For example, the association can comprise a chemical interaction, a physical interaction, a biological interaction, and/or a close-proximity spatial orientation.

In some embodiments, species and/or agents may associate via a chemical interaction, such as a chemical bond. The chemical bond may be a covalent bond or non-covalent bond. In some cases, the chemical bond is a non-covalent bond such as a hydrogen bond, ionic bond, dative bond, and/or a Van der Waals interaction. One or more of the species and/or agents may comprise functional groups capable of forming or configured to form such bonds. It should be understood that covalent and non-covalent bonds between components may be formed by any type of reactions, as known to those of ordinary skill in the art, using the appropriate functional groups to undergo such reactions. Chemical interactions suitable for use with various embodiments described herein can be selected readily by those of ordinary skill in the art, based upon the description herein.

In some embodiments, an association between species and/or agent(s) may occur via a biological binding event (i.e., between complementary pairs of biological molecules). For example, a species or agent may include an entity such as biotin that specifically binds to a complementary entity, such as avidin or streptavidin, on another species or agent. Other examples of biological molecules that may form biological bonds between pairs of biological molecules include, but are not limited to, proteins, nucleic acids, glycoproteins, carbohydrates, hormones, and the like. Non-limiting examples include, but are not limited to, an antibody/peptide pair, an antibody/antigen pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a receptor/hormone pair, a receptor/effector pair, a ligand/cellular receptor pair, a biotin/avidin pair, a biotin/streptavidin pair, a drug/target pair, small molecule/peptide pair, a small molecule/protein pair, and a small molecule/enzyme pair. Biological interactions between species and/or agent(s) for use in the embodiments described herein can be selected readily, by those of ordinary skill in the art, based upon the description herein as their function, examples of such biological interactions, and knowledge herein and in the art as to simple techniques for identifying suitable biological interactions.

In certain embodiments, species and/or agents may be associated with each other via a physical interaction. For example, in some embodiments, a species (e.g., supramolecular structure) may be physically entangled with at least a portion of another species or an agent (e.g., macromolecule). In some embodiments, the species or agent may be physically entangled with at least a portion of the other species or agent.

As mentioned above, at least a portion of a surface of a semiconductor nanosensor may be functionalized such that a species capable of participating or configured to participate in a molecular binding event is bound, directly or indirectly, to the surface. Non-limiting examples of such a bound species include antibodies, nucleic acids, antigens, small molecules, macromolecules, and molecules described herein for the target species. In general, the species bound to a portion of the surface of the semiconductor nanosensor can be any suitable molecule that can undergo a molecular binding event with another species with high specificity and/or affinity. The table in FIG. 9B provides a list of exemplary species that may be bound to one or more surfaces of a semiconductor nanosensor and are capable of undergoing a molecular binding event with a target species. Disassociation constants ($K_d$) are indicated to demonstrate the strength of molecular binding with these entities.

In some embodiments, a polyclonal or monoclonal antibody may be bound to a surface and used for detection of a target species. In some such cases, the method resembles an enzyme linked sandwich immunoassay (ELISA) in that serial additions of reagents are used to build increases in specificity and alter the magnitude of the signal strength. In the devices shown here in FIG. 1, the target species is directly bound to the sensor surface by high affinity with immobilized antibody. However, lower affinity interactions often can occur, limiting the specificity of detection.

In some embodiments, aptamers may be bound to a surface and used for detection of a target species. In general, an aptamer may have similar high affinity binding to selected target species governed by particular epitope of the target species as antibodies and aptamers can adopt three-dimensional conformations in solution. Therefore, aptamers may similarly be used as specificity elements bound to one or more surface of the nanosensors.

In principle, any proteins having an ability to specifically recognize another protein may be used as a specificity element in the context of the nanosensor surfaces. It is important to note that specificity elements have differing molecular properties and contribute to electrical properties forming conductance changes differently. Some examples of these are indicated in FIG. 8 although many association types may be assumed to be featured in a similar way according to certain embodiments. Common associations between proteins and ligands are categorized as protein: protein or protein:ligand (cofactor) associations and are represented with differing strengths of binding, often described in the form of disassociation constants ($K_d$). Notably, different protein:protein associations will exhibit differing strengths of binding even though these are each deemed to be 'specific' associations.

In some embodiments, selected proteins may be added to the nanosensor surface, and detection of these proteins may be conducted in reverse where antibodies, or antibody-containing solutions such as blood, serum, synovial fluid, cerebrospinal fluid, sputum, tumor lysates, ascites, and the like, are added for the purpose of detection and quantitation.

In certain embodiments, at least a portion of the surface of the semiconductor nanosensor may be functionalized to allow for direct or indirect binding of a species capable of participating or configured to participate in a molecular binding event. In some embodiments, the bound species may be directly bound to the surface of the semiconductor nanostructures, e.g., through conjugation chemistry of physical absorption. In other instances, the species is indirectly bound to the surface of the semiconductor nanosensor. For instance, the bound species may be directly bound to another species that is directly bound to the surface of the semiconductor nanosensor. Those of ordinary skill in the art will be knowledgeable of techniques for surface functionalization of a semiconductor surface that would allow a species to be bound, directly or indirectly. Non-limiting examples include surface treatment methods (e.g., etching, plasma treatment, corona treatment), physical absorption, conjugation chemistry, receptor ligand interactions (e.g., biotin and streptavidin).

In certain embodiments, species and/or agent(s) may be associated with each other or the surface of the semiconductor nanosensor via a linking moiety (e.g., other species and/or agent(s)) that causes the species and/or agent(s) to be in close proximity to another species, agent, and/or the surface of the semiconductor nanosensor. For example, the shortest distance between species and/or agent(s) associated with each other may be less than a Debye length. In some instances, the shortest distance may be less than or equal to about 100 nanometers, less than or equal to about 50 nanometers, less than or equal to about 25 nanometers, less than or equal to about 10 nanometers, or less than or equal to about 1 nanometers. In general, a species and/or agent(s) may be directly associated with each other or indirectly associated with each other.

For sensing, the Debye length determines the range of influence of the field effect in the solution. As the salt and solute concentration in the buffer solution is increased the Debye length gets shorter. Conversely, by reducing the salt concentration, the range of influence can be extended. In some embodiments, the salt concentration is adjusted so that the Debye length is approximately 10 nm, so that the nanosensors are sensitive to binding events within that range of the surface, but not sensitive to fluctuations deeper into the solution. Therefore, in implementing molecular interactions where specificity and signal amplification are important to the measurements, the distances from the silicon surface must be taken into consideration in the design and operation of the device. Macromolecules in solution can be in contact with counterions. As an example, DNA, which has a negative charge, can be surrounded by positively charged counterions in solution. Similarly, many proteins have a negative charge and are surrounded by positively charged counterions, although other proteins will be positively charged, and thus will be surrounded by negatively charged counterions. The Debye length is a scale that represents the relationship between electrostatic potential of the molecules and distance from the surface. As a result, charges of the macromolecule decay exponentially toward zero with increasing distance from the surface.

In some embodiments, the distances disclosed herein are approximately 2-12 nm (i.e., from the surface of the nanosensor to the end of the complex) corresponding to DNA and receptor protein sizes. However, several factors can contribute to whether the charge of a macromolecule contributes to a change in electrostatic potential of a target species detection strategy on a surface. These factors include solution ionic strength, charge of the macromolecule, and distance. Therefore, in some embodiments, it is possible to exceed the approximation of Debye length of 10 nm, especially where the electrical effect of the addition is large. Thus, certain embodiments describe the process to cause significant changes to the electrical properties at the surface of the nanosensors, despite the Debye length constraints. FIG. 9 is lists several features of macromolecules that are considerations in their use in diagnostic assays, according to certain embodiments.

FIG. 6A (Left Panel), includes a diagram showing the binding of an antibody 200, to a surface-bound target species, according to some embodiments, which process can be sensitive conductance changing, provided that distances obey the Debye length. FIG. 6B (Right Panel) includes an exemplary diagram showing the binding of an antibody 200, to a surface-bound target species, where a second binding of 205 nanoparticles of increased size are loaded with metals containing intrinsic electrical properties. In FIGS. 6A-6B, 210 indicates a Debye length influence at 10 nM or less and 215 indicates a Debye length influence at >10 nm.

Properties, operation methods, and configuration of nanosensors suitable for use in association with the embodiments described herein are described, for example, in International Patent Publication No. WO 2011/017077 filed Jul. 27, 2010, entitled "Nanochannel-based Sensor System with Controlled Sensitivity" and having the inventors Mohanty et al., which is incorporated herein by reference in its entirety for all purposes. In some embodiments, the nanosensors are manufactured of a semiconductor such as silicon. Such nanosensors may be manufactured, according to certain embodiments, in a stepwise manner termed top-down lithography. In some embodiments, a silicon nanosensor can be fabricated using a silicon device layer on top of an insulating layer, as can be found, for example, in a "Silicon-on-Oxide" configuration (e.g., a "silicon-on-oxide" wafer). In some embodiments, a layer of $Al_2O_3$ is deposited using Atomic Layer Deposition followed by attachment of biomolecules. Following the formation of the base and insulating layers, the nanosensor surfaces can be modifiable in a selected manner to alter conductive properties further, as is described in different embodiments as the attachment of biomolecules for the recognition of other substances. In general, the features of the devices prior to use are as follows. In some embodiments, the nanosensors are connected electrically to a circuit. In a simplified description, each nanosensor can be read independently by connecting sensing circuitry to a source and drain electrode on the nanosensor. Furthermore, physical gate electrodes can be fabricated on or near the nanosensors (and, in some embodiments, electrically coupled to a nanochannel of the nanosensor) for controlled accumulation or depletion of surface charge carriers on the nanosensor.

In certain embodiments, the nanosensors are field-effect devices, i.e. their conductance is affected by a localized electric field related to the surface potential, or the surface charge density.

For example, the nanosensors described herein can be field effect transistor devices, according to certain embodiments. Field effect transistor (FET) devices include a large family of devices, including metal-oxide FET (also called Insulated Gate FET), junction FET, and Ion-Sensitive FET, among others. In some such devices, the conductance of charge carriers between a source electrode and a drain electrode can be modulated by a gate electrode. The nanosensors in this invention can have, according to certain embodiments, analogous source and drain electrodes. In some embodiments, the conductance can be modulated by applying a potential to a gate electrode and/or by changing the surface charge density upon binding of a functionalized molecule.

In some embodiments, a nanosensor or nanochannel may have at least one (e.g., at least two orthogonal) cross-sectional dimensions that is less than 1 micron, less than or equal to about 750 nm, less than or equal to about 500 nm, less than or equal to about 250 nm, less than or equal to about 100 nm, less than or equal to about 50 nm, or less than or equal to about 10 nm. In some instances, the nanosensor or nanochannel may be elongated. In other instances, the nanosensor or nanochannel need not be elongated. In general the nanosensor may have any suitable shape (e.g., substantially regular polygon, substantially irregular polygon, substantially, substantially circular). In some embodiments, the aspect ratio of the nanosensor or nanochannel may be at least about 5:1, at least about 10:1, least about 15:1, at least about 20:1, least about 30:1, at least about 40:1, or least about 50:1. In certain embodiments, one or more agents (e.g., amplification agent) or species can be used to increase the selectivity of the signal pertaining to an identified target species, relative to that of backgrounds imparted by other materials in the same specimen. Other materials in the specimen may include other proteins, cells, chemicals, noise, and additional types of non-specific associations or effects that are not part of the desired signal measurement.

One embodiment of a sensor array system includes a plurality of nanoelectronic sensors configured to produce a plurality of different responses from a single applied specimen. The array includes a plurality of sensors having functionalization including non-metallic organic and/or inorganic materials, such as a polypeptide, polymer, biomolecules, and the like. The array sensors can be configured to detect conductance, capacitive, impedance, electrochemical and other sensor properties.

A plurality of common detection strategies may be employed. A field of nanosensors may be greater than one. For example, in some embodiments, the field of nanosensors can include 10-100 nanosensors. In the method, a field of nanosensors may also refer to a manufactured unit or sub-array from a silicon wafer. In one set of embodiments, a field of nanosensors is functionalized with a common detection recognition property. In another embodiment, the sensor array is replicated in wells of multi-well plates (such as 96-well or 384-well configurations).

U.S. Provisional Patent Application Ser. No. 61/885,235, filed Oct. 1, 2013, and entitled "Methods for Increasing the Molecular Specificity of a Nanosensor" is incorporated herein by reference in its entirety for all purposes.

The following examples are intended to illustrate certain embodiments of the present invention, but do not exemplify the full scope of the invention.

Example 1

This example describes a sandwich ELISA performed on a semiconductor nanosensor, wherein horse radish peroxidase HRP in a sandwich format was used as the amplification agent. The use of an amplification agent tagged with HRP in a sandwich format serves two purposes. First, the specificity can be highly increased because two different sites of the antigen need to bind independently to the specific sites on the primary and secondary antibodies. Second, the use of HRP as an enzyme catalyzing the reaction of a suitable substrate with hydrogen peroxide changes the electrical potential drastically in vicinity to the sensing element, due in part to the redox potential and binding of the reaction product, as described herein. This can greatly amplify the signal due to binding of the antigen to the sensor enabling the detection of smallest concentrations of the biomarker of interest.

A nanosensor may contain a sensing element and a signal transducer which can provide a recognition signal of the presence of a specific substance. The sensing element can determine the specificity of the nanosensor and it can comprise an enzyme, antibody, nucleic acid, or other target species detecting molecules. The specific binding or reaction between the target and the receptor (or the sensing element) can introduce a signal that is then transduced and measured. Nanosensors can be configured for macromolecular recognition, such as with human cells of different types, viruses, and pathogenic organisms. Therefore, there is a far-reaching diagnostic utility in these devices ranging from applications towards human health, food safety, drug response, and personalized medicine.

Nanosensors may be categorized by the operational mechanism of the sensors. Although optical nanosensors using colorimetric, fluorescence, luminescence, and absorbance are industry and diagnostics standards, these strategies generally involve target labeling and amplification. Also, the instrumentation footprint necessary to sensitively read optically-based signals is large compared with that achievable with devices incorporating nanotechnologies and microelectronics. Thus, emerging technologies that improve the sensitivity, cost, instrumentation, or field applicability of nanosensors are beginning to be implemented. Mechanical nanosensors utilize mass loading during the recognition process, introducing a dynamic resonance frequency change or static deflection of the device. Electronic nanosensors measure the change of the capacitance or conductance of the device due to biological recognition.

In some embodiments, each nanosensor surface has an electrical conductance property, and changes to the conductance can be measured electrically. A designated sensor surface can be formed by precision manufacturing that is physically separated from other sensors (which can be similar or different) in the same device. The FET sensor can be connected to an electronic circuit, and in the operation of the device, the specific conductance of this sensor surface can be monitored. Therefore, operationally, many independent electronic circuits may be interrogated in a massively parallel manner.

FET nanosensors can be adapted for the measurement of biomolecules interacting with such a sensor surface (FIG. 1). The surface of FET nanosensors can be modified to selectively recognize specific target species. In the illustration of FIG. 1, antibodies are conjugated to the surface of the nanosensor as part of the manufacturing process. These antibodies can be selected for specific detection of a protein of interest. Molecular binding events between the target species and the antibodies on the nanosensor surface can cause changes to the nanosensor surface charge density and/or surface potential. In this manner, FET nanosensors can offer precision manufacturing and sensitive target species recognition. The differential conductance amplitude can be correlated to the target species concentration in the sample solution.

The sensor device may be configured to distinguish and detect a range of different target species by measurement of the responses of a plurality of nanosensors of the array. In one example, the target species comprise a plurality of proteins, nucleic acid, and other macromolecules that may be present in a bodily fluid, aerosol, soil extract, liquid, gaseous and other media. Small-size, low-power, electronic sensor arrays have applications in fields such as medical, industrial, environmental and security detection.

Certain embodiments involve the use of materials and strategies to increase the electrical conductance effect determined on a field effect transistor and its physical nature and properties. Suitable materials are of multiple different forms, but have in common an ability to increase signal either by enzymatic release of ions, by surface charge redistribution, magnification, or otherwise. According to certain embodiments, materials may also be used in multiple combinations or sequences where the objective is to heighten specificity of detection and/or the magnitude of the detection signal. In certain embodiments, there is an ability to combine the material specificity and sensitivity elements on a multiplexed surface. In this setting, individual nanosensors may be functionalized with multiple, independent detectors, but common specificity and sensitivity enhancement elements may be used.

Certain embodiments relate to the benefit of achieving molecular binding events of high specificity and sensitivity that are valuable for precise determinations of disease and risk conditions for medical diagnostics, and for many other applications in industry, health sciences, research and development, agriculture, and defense. Therefore, certain embodiments relate to methods that increase specificity and sensitivity properties. Generally speaking, there are many categories of biomolecules and chemicals that may be detected by these strategies.

Despite these important objectives, there are considerable limitations to direct sensing because of the abundance and heterogeneity of proteins in common fluids needed for diagnostics. Whereas functional concentrations of proteins in the bloodstream may vary from femtomolar to a micromolar ranges typically, the protein content of the blood is 6.6 g/dL to 8.7 g/dL normally, and thus in vast excess relative to specific proteins. Human serum albumin is the most abundant blood protein constitutes about 60% of the total protein in plasma. Human Serum Albumin is found normally at a concentration between 35 and 55 mg/mL. Immunoglobulins are also a major protein component of blood. Immunoglobulin G, IgG, represent about 75-80% of blood immunoglobulins.

For substances in solution the isoelectric point (pI) generally refers to the pH at which the sum of the concentrations of the positively charged species, weighted by charge value, is equal to the weighted sum of the concentrations of the negatively charged species. In the case that there is one species of each type, the isoelectric point can be obtained directly from the pKa values. Therefore, with buffers at neutral pH, proteins with a pI<pH have a net negative charge, and proteins with a pI>pH have a net positive charge. Protein pKa values can be determined in consideration of the folded state of the protein and the collective pKa values of the amino acids in the polypeptide chain.

In this experiment, the detection of cardiac Troponin I (catnip) in buffer solution was studied. Cardiac Troponin I (as well as T) is a diagnostic marker for myocardial infarction. Detecting it in patient's blood can help in differentiating a serious, life-threatening heart condition from unstable angina.

In order to reliably measure small concentrations of catnip, a highly specific and sensitive biomarker can be useful. Combining highly sensitive silicon nanowire nanosensors with the specificity of a sandwich ELISA can overcome limitations of ordinary silicon nanowire sensors. According to certain embodiments, it can solve the problem of so-called Debye screening of charged species bound to the nanowire by the high concentration of salt ions in serum. It would also increase the specificity due to the sandwich format, according to some embodiments.

Figure 11:
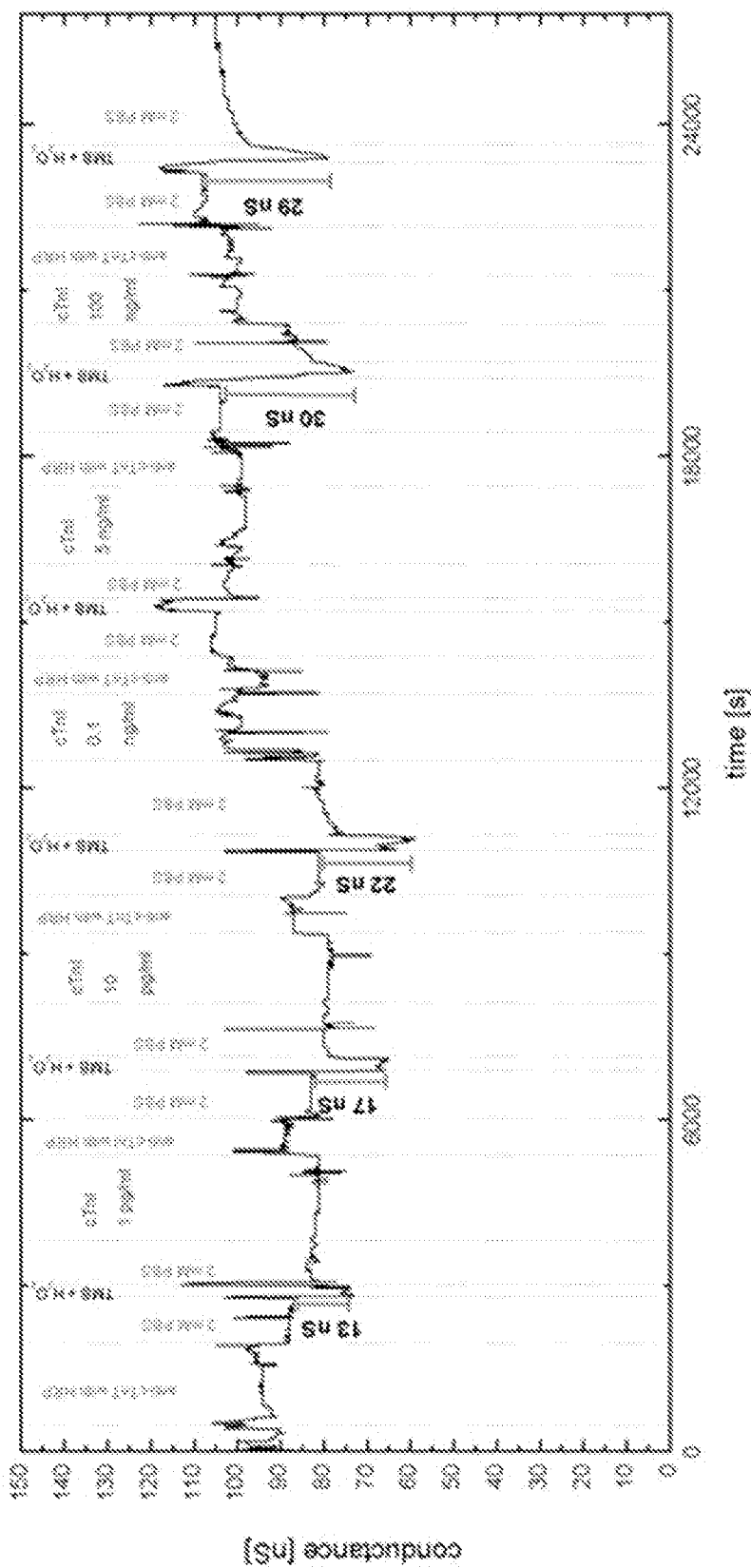
FIG. 11 is a real-time plot of conductance versus time, according to some embodiments, during a diagnostic assay.
Figure 12:
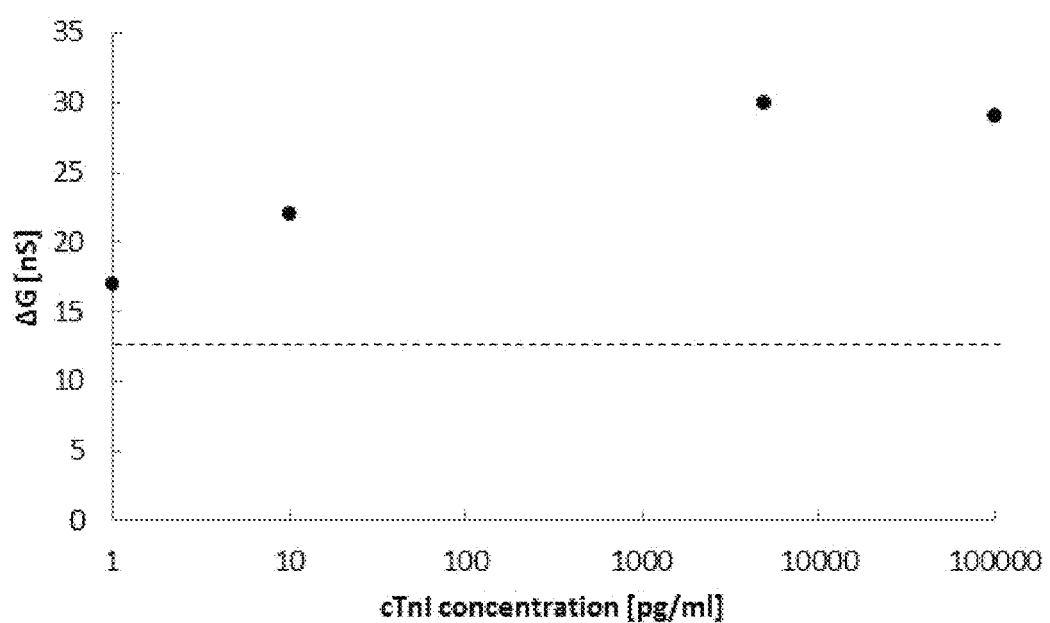
FIG. 12 is a plot of the signal versus the concentration of cardiac troponin, according to certain embodiments. In this exemplary plot, the dashed line indicates the baseline.

In this study chips with sets of 20 boron-doped silicon nanowires (cross section 200 nm×100 nm) functionalized with catnip antibodies were used. The chips were sealed in a fluid chamber and fluid was injected with a syringe pump. First, a base line was established by injecting a buffer solution containing the antibody tagged with HRP (AB- HRP) to the virgin chip and subsequently flushing the chip with 3,3',5,5'-tetramethylbenzidine (TMB) and hydrogen peroxide. Afterwards, the chip was washed with 2 mM PBS solution and then incubated with 1 pg/ml catnip in 2 mM PBS before it was flushed again with AB-HRP and then TMB and $H_2O_2$. This was repeated for several concentrations of catnip to establish a concentration dependence of the method. The real-time conductance data of the nanowire set is shown in FIG. 11. The corresponding concentration dependence is shown in FIG. 12.

FIG. 11 a plot of real-time conductance of one set of silicon nanowires as the chip is flushed with solutions containing the antibody, the antigen, the HRP-tagged antibody, and TMB and $H_2O_2$ (indicated in the graph).

Example 2

This is a prophetic example that describes the use of the procedure described above with respect to Example 1 with CA15.3 as the target antigen.

The procedure described above could also be used to measure the cancer biomarker CA15.3 as a target species. The nanosensor would be prepared with a capture antibody in a functionalization step. In the next step, an antigen-containing solution would be added, derived from blood, serum or other biological fluid that forms the specimen. After a wash step to remove unbound species, a second specific antibody would be added as a binding, which can also bind to the antigen and serve as a detecting agent. A secondary antibody may be added, capable of recognizing an epitope on the detection agent. As an example, for human cancer specimens, an "anti-human" secondary antibody would be selected. The secondary antibody would be conjugated to an enzyme, with examples being horseradish peroxidase, alkaline phosphatase, or glucose oxidase. In the presence of an appropriate oxidizable substrate, HRP can use hydrogen peroxide as an oxidizing agent to provide an enhanced or amplified electrical signal from the associated redox reaction and binding agents. This amplified electrical signal would be detected by the nanosensor. Examples of substrates include, but are not limited to, tetramethylenzidine, diaminobenzidine, or 4-chloronapthol.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system, comprising:
    an amplification agent associated with a first species capable of participating in a molecular binding event and at least three binding agents, wherein the binding agents comprise a metal; and
    a second species capable of participating in a molecular binding event associated with the first species, wherein the second species is associated with a surface of a semiconductor nanosensor.

2. The system of claim 1, wherein the amplification agent comprises at least 4 binding sites capable of participating in a molecular binding event with the binding agents.

3. The system of claim 1, wherein the first species is indirectly associated with the second species.

* * * * *